United States Patent [19]

Hiraga et al.

[11] 4,029,883

[45] June 14, 1977

[54] DEHYDROXYLATION OF AMINOSUGARS

[75] Inventors: Kentaro Hiraga, Kyoto; Tetsuya Okutani, Osaka; Kouichi Yoshioka; Tsunehiko Asako, both of Kyoto, all of Japan

[73] Assignee: Takeda Chemical Industries, Ltd., Osaka, Japan

[22] Filed: Dec. 20, 1973

[21] Appl. No.: 426,693

[30] Foreign Application Priority Data

| Dec. 29, 1972 | Japan | 48-2166 |
| Dec. 29, 1972 | Japan | 48-2167 |
| May 24, 1973 | Japan | 48-58282 |
| May 24, 1973 | Japan | 48-58283 |
| July 9, 1973 | Japan | 48-77261 |

[52] U.S. Cl. .................... 536/17; 424/180; 536/4; 536/10; 536/12; 536/14
[51] Int. Cl.² .................................... C07H 17/00
[58] Field of Search ... 260/210 AB, 210 K, 210 NE; 536/4, 10, 12, 14; 424/180

[56] References Cited

UNITED STATES PATENTS 3,721,664 3/1973 Hopper .................... 260/211.5 R
3,753,973 8/1973 Umezawa et al. ............. 260/210 K

OTHER PUBLICATIONS

Umezawa et al., Science 157, pp. 1559–1561, (1967).
Umezawa et al., J. of Antibiotics, vol. 24, No. 4, pp. 274–275, (1971).
Chemical Abstracts, vol. 79, p. 347, (76912a), (1973).
Houben and Wehyl, "Methoden der Organischen Chemie," 1964, pp. 187 & 255.
Wagner & Zook, *Synthetic Organic Chemistry*, 1953 Wiley and Sons Inc., New York, p. 8.

Primary Examiner—Lewis Gotts
Assistant Examiner—Cary Owens
Attorney, Agent, or Firm—Wenderoth, Lind & Ponack

[57] ABSTRACT

Dehydroxylation of aminoglycoside antibiotics is carried out by halogenation of phosphorylated aminoglycoside antibiotics followed by reduction of thus halogenated antibiotics. The dehydroxylation process is entirely new and gives the final product in a high yield. The resulting deoxyaminoglycoside antibiotics are effective against microorganisms including aminoglycoside antiobiotics-resistant microorganisms.

12 Claims, No Drawings

DEHYDROXYLATION OF AMINOSUGARS

This invention relates to novel processes of dehydroxylation of aminoglycoside antibiotics.

Hitherto, aminoglycoside antibiotics have frequently been used for treating infections caused by microorganisms. But, in the course of the administration of the anitibiotics, a number of microorganisms resistant to the antibiotics have appeared.

Recently, there have been several reports that deoxyaminoglycoside antibiotics are effective against these aminoglycoside antibiotics-resistant microorganisms.

As to dehydroxylation of aminoglycoside antibiotics, Journal of Antibiotics 21, 613–616 (1972) reports that 3',4'-dideoxyribostamycin is synthesized starting from ribostamycin through nine steps with at most 15% of overall yield;

Journal Antibiotics 24, 274–275 (1971) reports that 3'-deoxykanamycin is obtained by reacting 6-azido-2,4-di-O-benzyl-3,6-dideoxy-$\alpha$-D-glucopyranosyl chloride with 6-O-(2-O-benzyl-3-deoxy-3-ethoxycarbonylamido-4,6-O-isopropylidene-$\alpha$-D-glucopyranosyl)-N,N'-diethoxycarbonyl-2-deoxystreptamine in a yield of about 25%;

and in German Patent Application No. OLS-2,135,191 corresponding to U.S. Pat. No. 5,753,973 it is disclosed that 3',4'-dideoxykanamycin B is synthesized, but this process also gives the object compound in such a low yield of at most 20%.

In view of the disclosure in these literature references, the overall yields of the products obtained by the respective methods are by far lower than 25%.

Under these circumstances, the present inventors have made an extensive studied to find out an efficient process for dehydroxylation of aminoglycoside antibiotics, resulting in the discovery of novel processes for dehydroxylation of aminoglycoside antibiotics.

Thus, it is an object of this invention to provide an entirely new route for dehydroxylation of aminoglycoside antibiotics.

Another object of this invention is to provide a new method for production of dehydroxylated aminoglycoside antibiotics in a high yield.

A further object of this invention is to provide a new compound, halogeno-dehydroxylated-aminoglycoside antibiotics which is effective against aminoglycoside antibiotic-resistant microorganisms.

These and other objects of this invention will be apparent from the detailed description of this invention hereinafter provided.

The aminoglycoside antibiotics include neomycin type aminoglycoside antibiotics which have sugars at 4-and/or 5-position(s) of 2-deoxystreptamine such as neomycins (e.g. neomycin A, neomycin B, neomycin C, neomycin LPb, neomycin LPc), paromonycins (e.g. paromomycin I, paromomycin II), butirosins (e.g. butirosin A, butirosin B), ribostamycin, xylostasin, lividomycins (e.g. lividomycin A, lividomycin B) or of streptamine such as hybrimycins (e.g. hybrimycin $A_1$, hybrimycin $A_2$, hybrimycin $A_3$, hybrimycin $B_1$, hybrimycin $B_2$, hybrimycin $B_3$), kanamycin type aminoglycoside antibiotics which have sugars at 4- and 6-positions of 2-deoxystreptamine such as kanamycins (e.g. kanamycin A, kanamycin B, kanamycin C), 3',4'-dideoxykanamycin B, gentamycins (e.g. gentamycin $C_{1a}$, gentamycin $C_1$, gentamycin $C_2$, gentamycin A, gentamycin B, gentamycin $B_1$, gentamycin D), tobramycin, sisomicin, streptomycin type aminoglycoside antibiotics such as streptomycins (e.g. streptomycin, streptomycin B, dihydrostreptomycin), hydroxystreptomycin, bluensomycin, and other type aminoglycoside antibiotics such as destomycins (e.g. destomycin A, destomycin B), and hygromycin B.

The term "deoxyaminoglycoside antibiotic" means a compound derived by dehydroxylation of the starting aminoglycoside antibiotic. Therefore, the starting aminoglycoside antibiotics include deoxyaminoglycoside antibiotics as such, for example, monodexoyaminoglycoside antibiotics, and dideoxyaminoglycoside antibiotics.

In the present invention, phosphorylated aminoglycoside antibiotics are employed as starting materials which are obtainable by phosphorylation of aminoglycoside antibiotics.

The phosphorylation of aminoglycoside antibiotics is conducted by, for example, contacting the aminoglycoside antibiotics with a culture broth or a processed matter derived therefrom containing phosphotransferase of a microorganism belonging to, for example, *Pseudomonas aeruginosa* or *Escherichia coli* in the presence of a phosphate donor.

The typical examples of the said microorganism are *Escherichia coli* R11 (FERM-P 2123, ATCC-21990), *Escherichia coli* K12 ML 1629 [Journal of Antibiotics, 21, No. 1, 22–29 (1968)], *Escherichia coli* ML1401Rm$_{81}$ $^+$ [Antimicrobial Agents and Chemotherapy, 2, No. 3, 142–146 (1972)], *Escherichia coli* JR66/W677 [FEBS LETTERS 14, No. 5, 293 (1971)] and *Pseudomonas aeruginosa* R34R [FERM-P No. 2124].

The said microorganism is cultivated in a culture medium which comprises carbon sources such as glucose, sucrose and soluble-starch, nitrogen sources such as meat extract, yeast extract, corn-steep liquor, amino acids, ammonium sulfate, ammonium nitrate and ammonium chloride and inorganic compounds such as magnesium chloride and sodium chloride. The cultivation is conducted under static or aerobic stirred conditions. The cultivation temperature is 20° to 40° C, more preferably 28° to 37° C. PH of the medium used is 6 to 9, more preferably 6.8 to 7.8. The cultivation period is 2 to 72 hours, more preferably 6 to 24 hours.

The culture broth thus obtained or the processed matter derived therefrom containing phosphotransferase is used in the phosphorylation of aminoglycoside antibiotics. The processed matter is any and all materials having an aminoglycoside antibiotics-phosphorylation-activity obtained by processing the culture broth by, for example, filtration, centrifugation, sonication or disintegration by French press or lytic enzyme treatment of the culture broth.

The phosphorylation is carried out at 15° to 80° C, more preferably 30° to 40° C and within pH range 4 to 11, more preferably 6 to 10, for, in general, 10 minutes to 48 hours, more preferably 1 to 48 hours. Concentration of the starting aminoglycoside antibiotic in the reaction system is preferably 0.01 to 100 mg./ml. and the culture broth or the processed matter may be employed in an amount containing 1 to 50 parts in terms of wet mycelia per 1,000 parts by volume of the reaction system.

To the reaction system phosphate donor, reaction promotor and enzyme stabilizer may be added. But, in some cases the reaction does not necessarily require the addition of phosphate donor, because the cells or mycelia employed generally contain phosphor compounds which may act as phosphate donor.

Phosphate donor is exemplified by adenosine triphosphate, adenosine diphosphate, deoxyadenosine triphosphate, deoxyadenosine diphosphate, cytidinetriphosphate, guanosinetriphosphate and uridinetriphosphate. The reaction promotor is exemplified by potassium chloride, sodium chloride, ammonium chloride, lithium chloride, 2-mercaptoethanol, dithiothreitol, cystein. Enzyme stabilizer is exemplified by mannitol, sorbitol, glycerol, ammonium sulfate, and sucrose.

Further, metal salts such as magnesium chloride, magnesium sulfate, magnesium acetate, manganese chloride, cobalt chloride and zinc chloride, ferrous chloride ($FeCl_2$), nickel chloride ($NiCl_2$) may also be added to the reaction system, if desired.

By this phosphorylation, one or more hydroxyl groups of the aminoglycoside antibiotic are phosphorylated. The phosphorylated hydroxyl group is sometimes referred to as "phosphonoxy group" hereinafter. Positions of phosphonoxy groups vary with the types of aminoglycoside antibiotics and phosphorylation conditions, especially, kinds of phosphotransferase employed. The phosphonoxy group includes unsubstituted phosphonoxy group ($-OPO_3H_2$), substituted phosphonoxy groups such as nucleotidylphosphonoxy groups (e.g. adenosylphosphonoxy, uridylphosphonoxy, 5'-inosinylphosphonoxy, 5'-guanosylphosphonoxy), alkylphosphonoxy groups (e.g. dimethylphosphonoxy, diethylphosphonoxy, methylphosphonoxy, ethylphosphonoxy).

Separation of the phosphorylated aminoglycoside antibiotics thus obtained from the reaction mixture is conducted by a per se conventional manner such as extraction, precipitation, lyophylization and chromatography using a column packed with ion-exchange resin, ion-exchange cellulose or activated carbon.

The thus phosphorylated aminoglycoside is employed as the starting compound of the present invention, which is to be subjected to halogenation. Before the compound is subjected to halogenation, all of the functional groups, such as hydroxyl or amino groups, of the said phosphorylated aminoglycoside antibiotic should be protected by a suitable protective group such as a silyl group or an acyl group.

Protection of the functional groups is performed by reacting the phosphorylated aminoglycoside antibiotic with, for example, a silylating agent or acylating agent.

The above-mentioned silylating agent may for example be hexamethyldisilazane, trimethylchlorosilane, bis-(trimethylsilyl) acetamide, bis-(trimethylsilyl)-trifluoroacetamide, trimethylsilylacetamide, N-methyl-N-trimethylsilylacetamide, N-trimethylsilylimidazole, N-(trimethylsilyl)diethylamine or halosilane (e.g. dimethyldichlorosilane).

When the silylating agent is used, the reaction need not necessarily be conducted in a solvent, though a non-protonating solvent may be employed. The non-protonating solvent may for example be benzene, dimethylformamide, tetrahydrofuran, dioxane, acetonitrile or hexamethylphosphoramide. If desired, the reaction may be caused to proceed more advantageously by employing a tertiary amine, e.g. triethylamine, pyridine, diisopropylmethylamine, or triethylenediamine, as a catalyst. This silylating reaction is carried out at −50° to 200° C and, preferably, at 80° to 150° C, though it may be conducted at room temperature.

The required amount of the silylating agent is no more than the amount necessary for protecting all the functional groups, e.g. hydroxyl, amino and guanidino groups, of the starting compound, though an excess of the agent may be employed.

To protect all of the functional groups with acyl groups, the starting compound is reacted with, for example, acetic anhydride, acetyl chloride, benzoyl chloride, benzyloxycarbonyl chloride or the like.

While this reaction may be conducted in the presence or absence of a solvent, such solvents as pyridine, collidine, dimethylformamide, acetonitrile, hexamethylphosphoramide, etc. can be employed. If desired, the progress of the reaction may be improved by using a base as a catalyst. The base may for example be triethylamine, triethylenediamine or pyridine. This reaction is conducted at −50° to 200° C, preferably at 80° to 150° C.

The amount of the acylating agent may be no more than the amount required for protecting all the functional groups of the starting compound, although it may be used in excess.

The above silylating and acylating agents may also be used in combination or reacted one after the other so that they will be introduced into the functional groups of the starting compound.

The halogenating reaction is conducted by reacting the phosphorylated and protected aminoglycoside with a halogenating agent. The halogenating agent includes halosilanes, for example, trialkylsilyl halide (e.g. trimethylsilylchloride, dimethylt-butylsilyl chloride, trimethylsilyl bromide, dimethyldichlorosilane, trimethylsilyl iodide), triarylsilyl halide (e.g. triphenylsilyl chloride), arylalkylsilyl halide (e.g. phenyl dimethylsilyl chloride, methyldiophenylsilyl chloride), trialkoxysilyl chloride (e.g. trimethoxysilyl chloride, triethoxysilyl chloride), thionyl chloride, trimethoxymethylphosphonium iodide, phosphorus oxychloride, phosphorus thiooxychloride, phosphorus pentachloride, oxalyl chloride, phosphorus pentabromide and so on.

The amount of halogenating agent may be equimolar to the compound obtained by the reaction just described, although it is more usual to employ an excess of the agent. One may use a mixture of such agents. This reaction is conducted at from −50° to 200° C and, for better results, at from 80° to 150° C. While the reaction may be conducted in the absence of a solvent, a non-protonating solvent may be employed, if desired. The non-protonating solvent may for example be pyridine, benzene, dimethylformamide, tetrahydrofuran, dioxane, hexamethylphosphoramide or acetonitrile. If desired, the reaction may be conducted more advantageously by adding a phosphine [for example, triarylphosphine (e.g. triphenylphosphine), trialkylphosphine (e.g. tri-n-butylphosphine)], or metal halide (e.g. zinc chloride, lithium chloride, aluminum chloride, boron trifluoride, titanium to the mixtures chloride).

When halosilanes are used as the halogenating agent, both the protection and the halogenation proceed simultaneously.

The halogenation proceeds very smoothly when the phosphorylated aminoglycoside has the following structural configuration:
 i. Phosphonoxy group is bound with secondary carbon atom,
 ii. The carbon atom is bound with a carbon atom having a primary or secondary amino group, and iii. The amino group and the phosphonoxy group take the trans-configuration to each other.

or when the phosphorylated aminoglycoside has the phosphonoxy group which is bound with a primary carbon atom. As the said phosphorylated aminoglycoside, type examples are neomycin type antibiotics having phosphonoxy group(s), at 3'- and/or 5''-positions, kanamycin type antibiotics having phosphonoxy groups at 3'- and/or 2''-position(s) and streptomycin type antibiotics having phosphonoxy group(s) at 3''-position.

The above finding regarding the halogenation was made by the present inventors for the first time and this finding is to be applicable to halogenation of all the aminosugar compounds.

The thus obtained halogenodeoxy aminoglycoside is a novel compound, which is useful as an intermediate for preparing the deoxyaminoglycoside as well as an antibiotic, as such, effective against not only usual microorganisms but also aminoglycoside antibiotic-resistant microorganisms.

The halogenodeoxyaminoglycoside is then subjected to reduction. The reduction is conducted by the manner per se known, such as catalytic reduction, electrolytic reduction, reduction using a reducing agent and reduction using a Grignard reagent.

When the reduction is practiced by catalytic reduction, i.e. by reduction in the presence of a catalyst, the following procedure may be followed. Thus, halogenodeoxyaminoglycoside is first dissolved in a routine solvent [e.g. water, alcohol (e.g. methanol, ethanol, isopropanol, etc.), acetone, dioxane, tetrahydrofuran, dimethylformamide or a mixture of such solvents] and hydrogen gas is bubbled into the solution in the presence of a catalyst (e.g. Raney nickel, palladium-on-carbon, palladium-barium carbonate, platinum oxide, rhodium complex, Raney type catalyst of cobalt, Raney type catalyst of iron, Raney type catalyst of copper). This reaction is carried out at a temperature of from −30° to 150° C, desirably at from room temperature to 100° C. While the reaction proceeds readily at atmospheric pressure, one may conduct it at elevated pressures between 5 and 100 kg/cm². The reaction may be hastened and, depending upon the particular type of starting compound, the yield of the contemplated product may be enhanced by adding a suitable base to the reaction system, examples of said base including triethylamine, diethylamine and alkali metal hydroxide. When electrolytic reduction is used, the starting compound is dissolved in a suitable solvent and then the routine procedure is applied. For example, the halogenodeoxyaminoglycoside is dissolved in a solvent [e.g. water, alcohol (e.g. methanol, ethanol, etc.), ammonia, dimethylformamide, etc.] and the reduction is carried out using a low overvoltage electrode (e.g. platinum, wolfram, etc.) or a high overvoltage electrode (e.g. lead, zinc, mercury, etc.). Better results are sometimes obtained when the pH of the solution is brought to the acid side, for example to pH 2–3.

When the reduction is to be practiced employing a reducing agent, the halogenodeoxyaminoglycoside is treated with a reducing agent [for example, a metal hydride (e.g. lithium aluminum hydride, sodium borohydride, tributyltin hydride, etc.), alkali metal (e.g. lithium, sodium, etc.), a metal salt (e.g. divalent chromium salts such as chromous chloride, chromous acetate, etc.) or zinc or amalgamated zinc] in a suitable solvent (e.g. methanol, ethanol, t-butanol, amylalcohol, dimethylformamide, dioxane, tetrahydrofuran, dimethylsulfoxide, ethylene glycol, ethylenediamine, diethylenetriamine, etc.). The method is practiced at a temperature of from −30° to 150° C and, for better results, at room temperature to 80° C.

When a Grignard reagent is employed, the following procedure is followed. Thus, the halogenated antibiotic, either as such or after it has been treated so as to mask all its functional groups, is treated with magnesium metal in a solvent which is routinely used in Grignard reactions, e.g. tetrahydrofuran, ether or dioxane, and the resultant Grignard reagent is decomposed with water, methanol, ethanol, n-butanol or the like at room temperature or, if required, under heating, whereby the halogen is replaced by hydrogen.

The protective groups may be removed before, at the same time as or after the reduction.

Removal of the silyl groups can be easily effected by contacting the product with a proton donor such as water, alcohol (e.g. methanol, ethanol, etc.) carboxylic acid (e.g. acetic acid, propionic acid, etc.) or sulfonic acid (e.g. p-toluenesulfonic acid). Removal of the acyl groups can be performed with ease by hydrolyzing the product with, by way of catalyst, an acid (e.g. hydrochloric acid, sulfuric acid, etc.) or an alkali (e.g. sodium hydroxide, barium hydroxide, potassium hydroxide, etc.).

Thus, the desired deoxyaminoglycoside is produced. The dehydroxylated position of the deoxyaminoglycoside is coincides with the position of the phosphonoxy group of the starting compound.

Some of the deoxyaminoglycoside antibiotics obtainable by the method of this invention are per se known compounds, but the following are new compounds: 3'-deoxyneomycin B, i.e. 0-[α-2,6-diamino-2,3,6-trideoxy-D-glucopyranosyl (1 → 4)] 0-(0-{α-2,6-diamino-2,6-dideoxy-L-idopyranosyl (1 → 3)}-β-D-ribofuranosyl (1 → 5)] 2-deoxystreptamine, 3'-deoxyxylostasin, i.e. 0-β-D-xylofuranosyl-(1 → 5)-0-[α-2,6-diamino-2,3,6-trideoxy-D-glucopyranosyl (1 → 4)]-2-deoxystreptamine, and 3'-deoxyribostamycin, i.e. 0-β-D-ribofuranosyl (1 → 5)-0-[α-2,6-diamino-2,3,6-trideoxy-D-glucopyranosyl (1 → 4)]-2-deoxystreptamine.

Separation and purification of the desired-deoxyamino glycoside antibiotics can be produced by routine procedure such as extraction, precipitation, lyophylization, and ion-exchange column chromatography on a weakly acid resin.

The halogenodeoxyaminoglycoside antibiotics and deoxy aminoglycoside antibiotics both have substantially the same antibacterial activities as those of the corresponding aminoglycoside antibiotics, and, they are also effective against those bacteria which are resistant to the aminoglycoside antibiotics. Therefore, the thus obtained deoxyaminosugar compounds are useful as antituberculotics, antidysenterics or anti-staphylococcal drugs.

The deoxy aminoglycoside antibiotics or halogenodeoxyaminoglycoside antibiotics may be usually administered in such dosage forms as tablets, injections and so on together with excipients in the daily routine dosage of 1 to 30 mg./kg. to mammals, e.g. human being, bovine, pig or rat. For example, 3'-deoxyneomycin B is used in the form of tablets in the daily routine dosage of about 4 mg./kg. 3'-deoxyxylostasin is used in a form of injections in the daily routine dosage of about 20 mg./kg. per mammal and 3'-deoxyribostamycin is used in a form of injections in the daily routine dosage of about 20 mg./kg.

For further explanation of the present invention, the following examples are given, wherein "part(s)" are based on weight unless otherwise noted and the relationship between "part(s)" and "part(s) by volume" corresponds to that between "gram(s)" and "milliliter(s)". The terms "M", "N", "%" and "r.p.m." mean molar concentration, normality or equivalent concentration, percent and revolution(s) per minute, respectively. Resins named "Amberlite" are products manufactured by Rohm and Haas Company, Ltd. in the U.S.A.

REFERENCE EXAMPLE 1

In 250 parts by volume of an 0.5N aqueous solution of barium hydroxide is dissolved 5.0 parts of butirosin A. The solution is refluxed for 2 hours and then cooled. The solution is neutralized with 1N sulfuric acid. The resulting precipitate of barium sulfate is removed off by centrifuge. The supernatant fluid is run onto a colume of 300 parts by volume of cation exchange resin (Amberlite CG-50($NH_4^+$-form) (Rohm and Haas Co.)). The colume is washed with water and eluted with 0.2N aqueous ammonia. Fractions containing xylostasin which is detected by thin layer chromatography are pooled and concentrated under reduced pressure to dryness and lyophilized, whereby 3.8 parts of xylostasin as white powders are obtained.

Elemental analysis for $C_{17}H_{34}H_4O_{10}$: Found: C, 44.23%, H, 7.35 %; N, 12.10%. Calculated: C, 44.93%; H, 7.54%; N, 12.33%.

Optical rotation: $[\alpha]_D^{21} = 34°$ (c=1 in water).

The chemical name of xylostasin is 0-β-D-xylofuranosyl(1 → 5)-0-(α-2,6-diamino-2,6-dideoxy-D-glucopyranosyl(1 → 4)]-2-deoxystreptamine and the chemical structure of xylostasin is as follows;

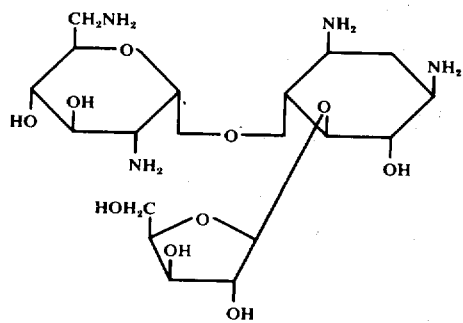

REFERENCE EXAMPLE 2

A liquid medium (ph 7.2) containing 3% of polypepton (pancreatic digest of casein) (manufactured by Daigo Nutritive Chemicals Ltd.), 1% of meat extract, and 0.5% of sodium chloride is inoculated with Bacillus sp. Y-399 which has been deposited under the accession numbers of ATCC-21932 at the American Type Culture Collection in Maryland, U.S.A. and of FERM-P No.1479 at the Fermentation Research Institute, Agency of Industrial Science and Technology, in Chiba, Japan.

The cultivation was carried out under shaking at 28° C for 40 hours. This seed culture was then inoculated to an aqueous culture medium (30,000 parts by volume, pH 7.5) which comprises 1% of glucose, 1% of polypepton, 0.7% of meat extract and 0.5% of magnesium chloride in a tank (50,000 parts by volume capacity) at an inoculum size of 10% and the cultivation was carried out at 28° C, 100% aeration and 200 r.p.m. for 66 hours.

The resultant fermentation broth was adjusted to pH 1-2 with a saturated aqueous solution of oxalic acid and, then, filtered with a filter aid (300 parts of HyfloSuper-Cel(Johns-Manville Products Co.)]. The filtrate was adjusted to pH 7 and passed through a column packed with 2,000 parts by volume of cation exchange resin [Amberlite IRC-50 ($NH_4^+$-form)], whereupon the active product active against Bacillus subtilis PCI 219 was adsorbed on the ion exchange resin. The resin was first washed with water and, then, eluted with 5% aqueous ammonia. The active fractions (2,500 parts by volume) were pooled and run onto a column of 600 parts by volume of a chromatographic grade of activated carbon to adsorb the active compound. The carbon column was washed with water and, then, eluted with an 0.3N hydrochloric acid. The active fractions were pooled, neutralized with anion exchange resin [Amberlite IR 45 (Rohm and Haas Co., $OH^-$-form)] and concentrated under reduced pressure. Finally, the concentrate was lyophilized to obtain 5.6 parts of a crude powder containing about 30% of xylostasin.

The crude product (5.6 parts) obtained as in the above procedure was dissolved in water and adsorbed on a column of 100 parts by volume of cation exchange resin [Amberlite CG-50(Rohm and Haas Co., $NH_4^+$-form)]. After washing with water, the column was eluted with 0.2N aqueous ammonia. The active fractions were collected and concentrated under reduced pressure. Ten times of acetone (v/v) was added to the concentrate and the resultant precipitates were collected by filtration. The procedure yielded 1.8 part of a pale-yellow powder (xylostasin content: about 90%). This powder was dissolved in water and adsorbed on a column of 200 parts by volume of cation exchanger [CM-Sephadex C-25 ($NH_4^+$-form)]. The column was then eluted with aqueous ammonia using the technique of gradient elution (from 0 to 1.7N) and the active fractions containing xylostasin alone were pooled and concentrated to dryness under reduced pressure, whereupon 1.41 part of a white xylostasin powder was obtained.

EXAMPLE 1

A mixture of 1.0 part of xylostasin-3'-phosphate monohydrate whose preparation will be mentioned below, 0.7 part of triphenylphosphine, 9 parts by volume of trimethylsilyl chloride, 4 parts by volume of hexamethyldisilazane and 7.5 parts by volume of pyridine is heated at 110° C for 43.5 hours. To 200 parts by volume of methanol is added the reaction mixture under ice cooling, followed by concentration under reduced pressure to dryness. To the residue is added 200 parts by volume of distilled water. The insolubles are collected by filtration and dissolved in 100 parts by volume of ethyl acetate, followed by washing with 100 parts by volume of water by shaking. The aqueous layer is concentrated under reduced pressure and combined with the filtrate. The mixture is run onto a column of 185 parts by volume of cation exchange resin [Amberlite IRC-50($NH_4^+$-form)]. The column is washed with 130 parts by volume of water and eluted with 1,000 parts by volume of 1N $NH_4OH$. The eluate is concentrated to about 100 parts by volume under reduced pressure, which is then run onto a column of 275 parts by volume of cation exchange resin [Amberlite CG-50($NH_4^+$-form)] to adsorb.

The column is washed with water and, then, fractionated by linear gradient method with 1,000 parts by volume of distilled water and 1,000 parts by volume of 0.3N aqueous ammonia. The fractions containing 3'-chloro-3'-deoxyxylostasin are combined and concentrated under reduced pressure to dryness and lyophilized, whereupon 0.05 part of 3'-chloro-3'-deoxyxylostasin dihydrate is obtained.

Elemental analysis for $C_{17}H_{33}N_4O_8Cl \cdot 2H_2O$: Calcd.: C, 40.12; H, 7.33; N, 11.01; Cl, 6.97. Found: C, 40.08; H, 7.29; N, 10.73; Cl, 6.55.

Optical rotation: $[\alpha]_D^{24} = 29.7°$ (c=0.6 in water).

Rf value was 0.41 on a thin layer chromatography using silica gel glass plate (Art.5721, sold by Merck & Co.) in a solvent system which contained 5 parts by volume of the upper layer of $CHCl_3:CH_3OH$:aqueous ammonia:water (4:3:2:1) and 3 parts by volume of methanol, while that of free xylostasin employed as the control was 0.23.

The starting material xylostasin-3'-phosphate is obtained by phosphorylation by the use of an enzyme from *Escherichia coli* No.R11(FERM-P No.2123, ATCC-21990).

Two hundred parts by volume of an aqueous seed culture medium (pH 7.2) comprising 0.5% of yeast extract, 0.5% of polypepton, and 0.3% of meat extract in inoculated with *Escherichia coli* R11. The cultivation is carried out under shaking at 37° C for 16 hours. This seed culture is then inoculated to an aqueous main culture medium (1,800 parts by volume, pH 7.2) having the same composition as the above and the cultivation is carried out under shaking at 37° C for 4 hours. The culture broth is subjected to centrifuge to recover 4.4 parts of wet cells. The cells are suspended into 17.6 parts by volume of 0.05M phosphate buffer (ph 7.0).

The suspension is subjected to ultrasonic oscillation (Kaijo Denki Co., Ltd.T-A-4201, 4280-type, 2A) to disintegrate the cells, followed by removing the debris (insoluble materials) by centrifuge, whereby 17 parts by volume of crude enzyme solution is obtained.

To 17 parts by volume of the crude enzyme solution are added 5 parts of xylostasin, 50 parts by volume of 0.5M phosphate buffer (pH 7.0), 100 parts by volume of 1M adenosine triphosphate solution, 50 parts by volume of 0.1M magnesium acetate solution and 50 parts by volume of 0.1M 2-mercapto ethanol, which is filled up to 500 parts by volume with distilled water. The mixture is subjected to enzymic reaction at 37° C for 20 hours.

The reaction mixture is heated at 80° C for 5 minutes to cease the reaction, followed by centrifuge. The supernatant is run onto a column of 900 parts by volume of cation exchange resin [Amberlite IRC-50($NH_4^+$-form)]. The column is washed with water and eluted with 1N aqueous ammonia to give fractions which contain xylostasin-3'-phosphate. The fractions are collected and concentrated and run onto a column of 150 parts by volume of cation exchange resin [Amberlite CG-50($NH_4^+$-form)].

The column is washed with water, and is fractionated by the linear gradient elution with 1,200 parts by volume of distilled water and 1,200 parts by volume of 0.2N aqueous ammonia. Fractions which include xylostasin-3'-phosphate are collected, concentrated under reduced pressure and lyophilized, whereby 4.4 parts of xylostasin-3'-phosphate monohydrate is obtained as a white powder.

Elemental analysis for $C_{17}H_{35}N_4O_{13}P \cdot H_2O$: Calcd.: C, 36.96; H, 6.75; N, 10.14; P, 5.61. Found: C, 37.52; H, 6.73; N, 9.78; P, 5.41.

Optical rotation: $[\alpha]_{D24} = 40.0°$ (c=0.60 in water).

IR $\nu_{max}^{KBr}$ $cm^{-1}$: 968.

Rf value was 0.55 on a thin layer chromatography using silica gel glass plate (Merck, Art.5721) in a solvent system which contained 5 parts by volume of the upper layer of $CHCl_3:CH_3OH:28\%$ ammonia: $H_2O$ (4:3:2:1) and 3 parts by volume of methanol, while that of free xylostasin employed as the control was 0.23.

For obtaining further accurate analytical values of the above product, it is acetylated to obtain tetra-N-acetylxylostasin-3'-phosphate dihydrate, which is subjected to elemental analysis.

Elemental analysis for $C_{25}H_{43}N_4O_{17}P \cdot 2H_2O$: Calcd.: C, 40.65; H, 6.41; N, 7.59; P, 4.19. Found: C, 40.95; H, 6.52; N, 7.70; P, 4.16.

In 20 parts by volume of water is dissolved 0.2 part of 3'-chloro-3'-deoxyxylostasin and with the addition of 2.5 parts by volume of Raney nickel and 0.3 part by volume of triethylamine, the mixture is shaken in hydrogen streams at atmospheric temperature and pressure. After 6 hours, the catalyst is filtered off. Then, the catalyst is washed well with 150 parts of volume of 1N aqueous ammonia and the washing is combined with the filtrate, followed by concentration to about 20 parts by volume. The resulting precipitates are removed by filtration, and the filtrate is run onto a column of 30 parts by volume of cation exchange resin (Amberlite CG-50 ($NH_4^+$-form)). The column is washed with water and eluted with 0 to 0.5N aqueous ammonia (gradient). Fractions which include 3'-deoxyxylostasin are pooled and concentrated under reduced pressure to dryness, whereby 0.152 part of 3'-deoxyxylostasin trihydrate is obtained.

Elemantal analysis for $C_{17}H_{34}N_4O_9 \cdot 3H_2O$: Calcd.: C, 41.54; H, 8.18; N, 11.37. Found: C, 41.23; H, 7.95; N, 11.08.

Optical rotation: $[\alpha]_D^{24} + 28.0°$(c=0.61 in water).

Rf value was 0.26 on a thin layer chromatography using silica gel glass plate (Merck, Art.5721) in a solvent system which contain 5 parts by volume of the upper layer of $CHCl_3:CH_3OH$ : aqueous ammonia:-water(4:3:2:1) and 3 parts by volume of methanol, while that of free xylostasin employed as the control was 0.23.

EXAMPLE 2

A mixture of 0.3 part of neomycin B-3'-phosphate pentahydrate, 2.7 parts by volume of trimethylsilyl chloride, 1.2 part by volume of hexamethyldisilazane, 2.25 parts by volume of dry pyridine and 0.21 part of triphenylphosphine is heated on an oil bath at 115° C for 44 hours. After the reaction has been completed, 30 parts by volume of methanol is added to the reaction mixture under cooling wth ice, followed by concentration under reduced pressure. To the concentrate is added 100 parts by volume of distilled water, and the insolubles are collected by filtration, to which are added 100 parts by volume of water and 100 parts by volume of ethyl acetate, followed by shaking. The water layer is concentrated under reduced pressure to remove ethyl acetate off. The aqueous layer is run onto column of 90 parts by volume of cation exchange resin [Amberlite IRC-50($NH_4^+$-form)].

The column is washed with 500 parts by volume of distilled water and, then, eluted with 300 parts by volume of 1N aqueous ammonia. The eluate is concentrated under reduced pressure, whereby 0.25 part of crude product is obtained. This is dissolved in 50 parts by volume of distilled water and adsorbed on 30 parts by volume of cation exchange resin [Amberlite CG-50I ($NH_4^+$-form)]. The resin is washed with 100 parts by volume of distilled water and fractionated by elution (gradient method) with 0–0.3N aqueous ammonia. The crude product thus obtained is further adsorbed on cation exchange resin [Amberlite CG-50($NH_4^+$-form)] and the resin is eluted with 0–0.3N aqueous ammonia. The eluate is concentrated under reduced pressure and lyophilized. The above procedure yields 0.195 part of 3'-chloro-3'-deoxyneomycin B dihydrate.

Elemental analysis for $C_{23}H_{45}N_6O_{12}Cl.2H_2O$: Calcd.: C, 41,28; H, 7.38; N, 12.55; Cl, 5.29. Found: C, 41.03; H, 7.29; N, 12.41; Cl, 5.35.

Rf value was 0.47 on a thin layer chromatography using silica gel glass plate (Art.5721, Merck) in a solvent system of a solution of $CHCl_3$:methanol:aqueous ammonia:water (1:4:2:1), while that of free neomycin B employed as the control was 0.29.

The starting material neomycin B-3'-phosphate pentahydrate has been prepared in a similar manner as described in The Journal of Antibiotics, 21, 22(1968), causing the crude enzyme solution of *Escherichia coli* K 12 ML 1629 to act upon neomycin B.

Specific rotation $[\alpha]_D^{24}=+63.3°(c=1.02$ in $H_2O)$.

Elemental analysis for $C_{23}H_{47}N_6O_{16}P.5H_2O$: Calcd.: C, 35.20; H, 7.32; N, 10.70. Found: C, 35.26; H, 7.05; N, 10.17.

UV: No specific absorbancy.

IR $\nu_{max}^{KBr}$ cm$^{-1}$: 958.

Rf value was 0.35 on a thin layer chromatography using silica gel glass plate (Art.5721, Merck) in a solvent system which contained 5 parts by volume of the upper layer of $CHCl_3$:$CH_3OH$:aqueous ammonia:water(4:3:2:1) and 3 parts by volume of methanol, while that of free neomycin B employed as the control was 0.11.

In 15 parts by volume of water is dissolved 0.1 part of 3'-chloro-3'-deoxyneomycin B and with the addition of 0.3 part by volume of Raney nickel and 0.5 part by volume of triethylamine, the mixture is shaken in hydrogen streams at atmospheric temperature and pressure. After 4 hours, the catalyst is filtered off. Then, the catalyst is washed well with 100 parts by volume of 1N aqueous ammonia and the washing is combined with the filtrate, followed by concentration. The procedure yields 0.085 part of crude powders. The crude product is dissolved in 20 parts by volume of distilled water and then adsorbed on a column packed with 35 parts by volume of cation exchange resin [Amberlite CG-50I ($NH_4^+$-form)] and the column is eluted witgh 0 to 0.5N $NH_4OH$ (gradient) and the eluate is concentrated under reduced pressure and lyophilized, whereupon 0.06 part of 3'-deoxyneomycin B dihydrate is obtained.

Elemental analysis ($C_{23}H_{46}N_6O_{12}.2H_2O$): Calcd.: C, 43.52; H, 7.94; N, 13.24. Found: C, 43.67; H, 7.75; N, 13.05.

Rf value was 0.36 on a thin layer chromatography using silica gel glass plate (Art.5721, Merck) in a solvent system of a mixture of $CHCl_3$:methanol:aqueous ammonia:water (1:4:2:1), while that of free neomycin B employed as the control was 0.29.

EXAMPLE 3

A mixture of 0.1 part of neomycin A-3'-phosphate trihydrate, 3 parts by volume of trimethylsilyl chloride, 3 parts by volume of bis(trimethylsilyl)acetamide and 3 parts by volume of dry pyridine is heated on an oil bath at 130° C for 15 hours. After the reaction has been completed, methanol is added to the reaction mixture under cooling with ice, followed by concentration under reduced pressure. The residue is dissolved in 50 parts by volume of distilled water, and the solution is run onto a column of 50 parts by volume of cation exchange resin [Amberlite IRC-50 ($NH_4^+$-form)]. The column is washed with 100 parts by volume of distilled water and, then, eluted with 200 parts by volume of 0.5N aqueous ammonia. The eluate is concentrated under reduced pressure to give 20 parts by volume of concentrate. This concentrate is adjusted to pH 7.0 and adsorbed on 20 parts by volume of cation exchange resin [Amberlite CG-50 ($NH_4^+$-form)].

The resin is fractionated by elution with 0.075N aqueous ammonia. The crude product thus obtained is further adsorbed on a column packed with 20 parts by volume of cation exchange resin [Amberlite CG-50 ($NH_4^+$-form)] and the column is eluted with 0.075N aqueous ammonia. The purified product is lyophilized. The procedure gives 0.035 part of 3'-chloro-3'-deoxyneomycin A.

Elemental analysis: ($C_{12}H_{25}N_4O_5Cl_1$): Calcd.: C, 42.29; H, 7.39; N, 16.44; Cl, 10.40. Found: C, 41.98; H, 7.13; N, 16.40; Cl, 10.12.

NMR $\delta_{ppm}^{D_2O}$: 5.47 (1H, d, J 1',2'=3 Hz, C 1'-H), 3.21 (1H, q, J 1',2'=3 Hz, J 2',3'=11 Hz, C 2'-H).

Rf value was 0.43 on a thin layer chromatography using silica gel glas plate (Chromagram 6060, Eastman Kodak) in a solvent system which contains 1 part by volume of the upper layer of $CHCl_3$:methanol:water:aqueous ammonia (2.0:1.5:0.5:1.0) and 1 part by volume of methanol, while those of free neomycin A and neomycin-3'-phosphate employed as the controls were 0.28 and 0.21, respectively.

For obtaining further accurate analytical values of the above product, it is acetylated and silylated to obtain tetra-N-acetyl-tri-O-trimethylsilylneomycin A-3'-phosphate, which is subjected to mass spectrum.

Characteristic peaks: 711($M^+$-$CH_3$) ($Cl^{37}$), 709($M^+$—$CH_3$)($Cl^{35}$), 673($M^+$—$CH_3$—HCl), 491, 463, 445, 419, 373, 355, 337, 299.

The starting material neomycin A-3'-phosphate trihydrate used has been prepared in a similar manner as described in The Journal of Antibiotics, 21, No.1, 22–29 (1968), causing the crude enzyme solution of *Escherichia coli* K 12 ML1629 to act upon neomycin A.

Elemental analysis for $C_{12}H_{26}O_9N_4P.3H_2O$: Calcd.: C, 31.65; H, 7.08; N, 12.30; P, 6.80. Found: C, 31.78; H, 7.22; N, 12.09; P, 6.81.

Ultraviolet ray absorption: No specific absorption.

NMR($D_2O$) $\delta$ : 3.14(2'-H), 401(3'-H), 5.78(1H,d,J=4Hz,1-H).

IR $\nu_{max}^{KBr}$ cm$^{-1}$: 965.

$[\alpha]_D^{27} = +95.17°$ (c=1.01 in water).

In 10 parts by volume of water is dissolved 0.15 part of 3'-chloro-3'-deoxyneomycin A and with the addition of 1.8 part by volume of Raney nickel and 0.2 part of triethylamine, the mixture is shaken in hydrogen streams at atmospheric temperature and pressure.

After 5 hours, the catalyst is filtered off. Then, the catalyst is washed well with 200 parts by volume of 1N NH₄OH and the washing is combined with the filtrate, followed by concentration. The insolubles are eliminated by filtration. The filtrate is then adsorbed on a column packed with 30 ml. of cation exchange resin [Amberlite CG-50I (NH₄⁺-form)] and washed with water and eluted with 0.1 to 0.5N NH₄OH(gradient) and purified, whereupon 0.12 part of 3'-deoxyneomycin A monohydrate is obtained.

Elemental analysis for $C_{12}H_{26}N_4O_5 \cdot H_2O$: Calcd.: C, 44.43; H, 8.69; N, 17.27. Found: C, 44.12; H, 8.53; N, 16.98.

Rf value was 0.35 on a thin layer chromatography using silica gel glass plate (Chromagram 6060, Eastman Kodak) in a solvent system which contained 5 parts by volume of the upper layer of CHCl₃:methanol:aqueous ammonia:water (4:3:2:1) and 3 parts by volume of methanol, while that of free neomycin A employed as the control was 0.30.

EXAMPLE 4

A mixture of 0.15 part of kanamycin B-3'-phosphate trihydrate, 7.5 parts by volume of trimethylsilyl chloride, 15.0 parts by volume of hexamethyldisilazane and 7.5 parts by volume of dry pyridine is heated on an oil bath at 130° C for 62 hours. After the reaction has been completed, methanol is added to the reaction mixture under cooling with ice, followed by concentration under reduced pressure. To the residue is added 100 parts by volume of distilled water, and the mixture is run onto a column of 200 parts by volume of cation exchange resin [Amberlite IRC-50 (NH₄⁺-form)]. The column is washed with 1,000 parts by volume of distilled water, and then, eluted with 1,000 parts by volume of 1N aqueous ammonia. The eluate is concentrated to dryness under reduced pressure to collect 0.12 part of crude product. This is dissolved in 50 parts by volume of distilled water and adsorbed on 30 parts by volume of cation exchange resin [Amberlite CG-50 (NH₄⁺-form)].

The resin is washed with 100 parts by volume of distilled water and fractionated by elution (gradient method) with 0–0.5 N aqueous ammonia. The crude product thus obtaned is further adsorbed on cation exchange resin [Amberlite CG-50 (NH₄⁺-form)] and the resin is eluted with 0–0.5 N aqueous ammonia. The purified product is lyophilized. The above procedure yields 0.082 part of 3'-chloro-3'-deoxykanamycin B monohydrate.

Elemental analysis for $C_{18}H_{38}N_5O_{10}Cl \cdot H_2O$: Calcd.: C, 41.57; H, 7.36; N, 13.46; Cl, 6.81. Found: C, 41.45; H, 7.56; N, 12.88; Cl, 6.64.

Optical rotation: $[\alpha]_D^{23}+106.5°$ (c=0.51, in water).

Rf value was 0.55 on a thin layer chromatography using silica gel glass plate (Art.5721, Merck) in a solvent system which contains 1 part by volume of the upper layer of CHCl₃:methanol:water:aqueous ammonia (2.0:1.5:0.5:1.0) and 1 part by volume of methanol, while those of free kanamycin B and kanamycin B-3'-phosphate employed as the controls were 0.39 and 0.25, respectively.

NMR $\delta_{ppm}^{D_2O}$: 5.44 (1H, d, J1',2'=3 Hz, C1'-H), 3.33 (1H, q, J1',2=3 Hz, J2',3'=10 Hz, C2'-H)

For obtaining further accurate analytical values of the above product, it is acylated and silylated to obtain penta-N-acetyl-penta-O-trimethylsilylkanamycin B-3'-phosphate, which is subjected to mass spectrum.

Characteristic peaks; 1056 (M-15), 1035 (M-36), 1020 (M-51), 838, 810, 689, 645, 599, 420, 361, 299.

The starting material kanamycin B-3'-phosphate trihydrate used has been prepared in a similar manner to that described in Applied Microbiology 16, No.9, 1276 (1968) causing the crude enzyme solution of *Pseudomonas aeruginosa* R34R (FERM-P No. 2124) to act upon kanamycin B.

Elemental analysis for $C_{18}H_{38}N_5O_{13}P \cdot 3H_2O$: Calcd.: C, 35.00; H, 7.18; N, 11.34; P, 5.01. Found: C, 35.23; H, 7.06; N, 10.99; P, 5.06.

Optical rotation: $[\alpha]_D^{23}=+108.6$ (c=0.53, in water).

NMR ($\delta$ in D₂O): 4.36(3'-H, quartet), 5.18(1''-H, doublet), 5.78(1'-H, doublet).

IR $\nu_{max}^{KBr}$ cm⁻¹: 970 (phosphate).

In a mixture of 1 part by volume of water and 1 part by volume of ethanol is dissolved 0.03 part of 3'-chloro-3'-deoxykanamycin B and with the addition of 0.5 part by volume of Raney nickel, the mixture is shaken in hydrogen streams at atmospheric temperature and pressure. After 3 hours, the catalyst is filtered off. Then, the catalyst is washed well with 50 part by volume of 1N aqueous ammonia and the washing is combined with the filtrate, followed by concentration. The procedure yields 0.025 part of crude powders. The crude product is then adsorbed on 5 part by volume of cation exchange resin [Amberlite CG-50(NH₄⁺-form)] and purified by elution with 0 to 0.5 N NH₄OH (gradient method), whereupon 0.02 part of 3'-deoxykanamycin B is obtained. This product is identical with an authentic sample.

For example, the following Rf values are obtained in thin layer chromatography.

1. E. Merck silica gel plate (Art.5721) (glass support)
   Solvent: The upper layer of CHCl₃-methanol-17 % NH₄OH(2:1:1).
   3'-chloro-3'-deoxykanamycin B: 0.78
   3'-deoxykanamycin B: 0.74
2. Eastman Kodak silica gel plate (Chromagram 6060) (synthetic resin support)
   Solvent: The upper layer of CHCl₃-methanol-conc. NH₄OH-water (20:53:10:5)
   3'-Chloro-3'-deoxykanamycin B: 0.64
   3'-Deoxykanamycin B: 0.58

Optical rotation $[\alpha]_D^{22}=+123.2°$ (c=1.085, in water).

Elemental analysis for $C_{18}H_{37}N_5O_9 \cdot 2H_2O$: Calcd.: C, 42.93; H, 8.20; N, 13.90. Found: C, 42.11; H, 8.04; N, 13.05.

The retention time of the corresponding trimethylsilyl derivative in gas chromatography is in complete agreement with that of an authenitc sample.

EXAMPLE 5

A mixture of 1.2 part of kanamycin B-3'-phosphate trihydrate, 0.8 part of triphenylphosphine, 10 parts by volume of trimethylsilyl chloride, 4 parts by volume of hexamethyldisilazane and 4 parts by volume of pyridine is heated at 130° C for 48 hours. The reaction mixture is added to 200 parts by volume of methanol under cooling with ice, which is concentrated under reduced pressure to dryness. The residue is dissolved in 300 parts by volume of distilled water. The solution is subjected to extraction with 120 parts by volume of methylene dichloride. The aqueous layer is recovered and the methylene dichloride still remaining is removed under reduced pressure. The aqueous layer is diluted with distilled water to 500 parts by volume as the total volume then the solution is run onto a column of 400 parts by volume of cation exchange resin [Amberlite IRC-50 ($NH_4^+$-form)]. The resin is washed with water and eluted with 1,400 parts by volume of 1N aqueous ammonia. The eluate is concentrated under reduced pressure to about 300 parts by volume and the concentrate is run onto a column of 160 parts by volume of cation exchange resin [Amberlite CG-50($NH_4^+$-form)].

The column is washed with water and is subjected to fraction-wise elution by the linear gradient method with 1,200 parts by volume of distilled water and 1,200 parts by volume of 0.3N aqueous ammonia. The eluate is concentrated under reduced pressure and lyophilized, whereby 0.755 part of 3'-chloro-3'-deoxykanamycin B dihydrate is obtained.

To a solution of 0.053 part of 3'-chloro-3'-deoxykanamycin B in 5 parts by volume of water was added 0.3 part by volume of Raney nickel and 0.1 part by volume of triethylamine and the mixture is shaken in hydrogen streams. After 4 hours, the catalyst is removed by filtration and washed with 50 parts by volume of 1N aqueous ammonia. The filtrate and washing are combined and concentrated. The residue is purified by chromatography on a column of cation exchange resin [Amberlite CG-50I ($NH_4^+$-form)], whereupon 0.033 part of 3'-deoxykanamycin B is obtained.

EXAMPLE 6

A mixture of 0.63 part of kanamycin B-3'-phosphate trihydrate, 5 parts by volume of trimethylsilyl chloride, 2 parts by volume of hexamethyldisilazane, 2 parts by volume of pyridine, 0.4 part of triphenylphosphine and 0.1 part of zinc chloride is heated at 100° C for 48 hours. The reaction mixture is treated in a similar manner to that of Example 4 whereby 0.425 part of 3'-chloro-3'-deoxykanamycin B is obtained.

To a solution of 0.1 part of 3'-chloro-3'-deoxykanamycin B in 10 parts by volume of water is added 0.3 part of palladium-on-carbon (1%). The system is stirred in hydrogen streams. After 5 hours, the catalyst is filtered off and washed with 50 parts by volume of 0.5N hydrochloric acid. The washing is combined with the filtrate and the combined solution is concentrated to about one-third of the original volume and, then, neutralized with 1N aqueous ammonia.

The neutralized solution is first desalted with cation exchange resin [Amberlite IRC-50($NH_4^+$-form)] and, then, purified on a column of 15 parts by volume of cation exchange resin [Amberlite CG-50I ($NH_4^+$-form)]. The procedure yields 0.064 part of 3'-deoxykanamycin B.

EXAMPLE 7

A mixture of 0.3 part of paromomycin I-3'-phosphate tetrahydrate, 2.7 parts by volume of trimethylsilyl chloride, 1.2 part by volume of hexamethyldisilazane, 2.25 parts by volume of dry pyridine, 0.21 part of triphenyl phosphine is heated on an oil bath at 110° C for 48 hours. After the reaction has been completed, the reaction mixture is poured into 30 parts by volume of methanol under ice-cooling, followed by concentration under reduced pressure. To the residue is added 100 parts by volume of distilled water, and the resulting precipitates are collected and subjected to extraction with 100 parts by volume of ethyl acetate. The aqueous layer is concentrated under reduced pressure. The concentrated aqueous layer is run onto a column of 90 parts by volume of cation exchange resin [Amberlite IRC-50 ($NH_4^+$-form)]. The column is washed with 500 parts by volume of distilled water and, then, eluted with 300 parts by volume of 1N aqueous ammonia.

The eluate is concentrated under reduced pressure, and the residue is dissolved in 50 parts by volume of distilled water and then run onto a column of 30 parts by volume of cation exchange resin [Amberlite CG-50I ($NH_4^+$-form)].

The column is washed with 100 parts by volume of distilled water and eluted fraction-wise with 0–0.3N aqueous ammonia (gradient method).

The crude product thus obtained is further adsorbed on cation exchange resin [Amberlite CG-50 ($NH_4^+$-form)] and the resin is eluted with 0–0.3N aqueous ammonia. Fractions which include 3'-chloro-3'-deoxyparomomycin I are combined and concentrated under reduced pressure, followed by lyophilizing the concentrate, whereby 0.202 part of 3'-chloro-3'-deoxyparomomycin I dihydrate is obtained.

Elemental analysis for $C_{23}H_{44}N_5O_{13}Cl\cdot 2H_2O$: Calcd.: C, 41.22; H, 7.22; N, 10.45; Cl, 5.29. Found: C, 40.97; H, 7.09; N, 10.73; Cl, 5.03.

TLC Rf value: 0.55 (plate: Art 5721, Merck).
Paromomycin I: 0.41.

(A solution of $CHCl_3$:methanol:aqueous ammonia:water = 1:4:2:1 is used as the developer).

The starting material paromomycin I 3'-phosphate tetrahydrate used has been prepared in a similar manner to that described in The Journal of Antibiotics, 21, 22 (1968), causing the crude enzyme solution of *Escherichia coli* K12ML to act upon paromomycin I.

Elemental analysis for $C_{23}H_{46}N_5O_{17}P\cdot 4H_2O$: Calcd.: C, 35.98; H, 7.09; N, 9.12. Found: C, 35.85; H, 7.02; N, 8.85.

Optical rotation $[\alpha]_D^{24} = +59.3°$ (c=1.01 in water).
Ultraviolet-ray absorption: No specific absorption.
IR $\nu_{max}^{KBr}$ $cm^{-1}$: 960.

Rf value was 0.46 on a thin layer chromatography using silica gel glass plate (Art.5721, Merck) in a solvent system contains 5 parts by volume of upper layer of $CHCl_3$:methanol:aqueous ammonia:water (4:3:2:1) and 3 parts by volume of methanol, while that of free paromomycin I employed as the control were 0.19.

In 20 parts by volume of water is dissolved 0.1 part of 3'-chloro-3'-deoxyparomomycin I and with the addition of 0.3 part by volume of Raney nickel and 0.5 part by volume of triethylamine, the system is shaken in hydrogen streams at atmospheric temperature and pressure. After 4 hours, the catalyst is filtered off. Then, the catalyst is washed well with 100 parts by volume of 1N aqueous ammonia and the washing is combined with the filtrate, followed by concentration to dryness. The procedure yields 0.091 part of crude powders. The crude product is dissolved in 20 parts by volume of distilled water and then the aqueous solution is run onto a column of 35 parts by volume of cation exchange resin [Amberlite CG-50I ($NH_4^+$-form)]. The column is eluted with 0–0.5N aqueous ammonia (gradient). The resulting fractions are concentrated under reduced pressure to dryness, whereupon 0.07 part of 3'-deoxyparomomycin I dihydrate is obtained. Elemental analysis for $C_{23}H_{45}N_5O_{13}\cdot 2H_2O$: Calcd.: C,43.45; H, 7.76; N, 11.01. Found: C, 43.29; H, 7.65; N, 10.91.

TLC Rf value: 0.47 (plate: Art 5721, Merck).
Control, paromomycin I: 0.41.

(A mixture of $CHCl_3$:methanol:aqueous ammonia:water = 1:4:2:1 is used as a developer.)

EXAMPLE 8 a mixture of 0.6 part of ribostamycin-5''-phosphate dihydrate, 0.6 part of triphenylphosphine, 5 parts by volume of trimethylsilyl chloride, 2 parts by volume of hexamethyldisilazane, 2 parts by volume of dry pyridine and 0.3 part of zinc chloride is heated at 110° C for 48 hours. After the reaction has been completed, 150 parts by volume of methanol is added to the reaction mixture under ice-cooling, followed by concentration to dryness under reduced pressure. The residue is shaken with 150 parts by volume of distilled water and 150 parts by volume of ethyl acetate. The aqueous layer is run onto a column of 130 parts by volume of cation exchange resin [Amberlite IRC-50($NH_4^+$-form)]. The column is washed with 1,500 parts by volume of distilled water and, then, eluted with 1,200 parts by volume of 1N aqueous ammonia. The eluate is concentrated to about 300 parts by volume under reduced pressure, which is run onto a column of 165 parts by volume of cation exchange resin [Amberlite CG-50 ($NH_4^+$-form)]. The column is washed and eluted with 1,000 parts by volume of distilled water and 1,000 parts by volume of 0-0.3N aqueous ammonia (gradient).

The resulting fractions are combined and concentrated to dryness and lyophilized, whereupon 0.247 part of 5''-chloro-5''-deoxyribostamycin monohydrate is obtained.

Elemental analysis for $C_{17}H_{33}N_4O_9Cl.H_2O$: Calcd.: C, 41.59; H, 7.18; N, 11.41; Cl, 7.22. Found: C, 41.43; H, 7.35; N, 11.25; Cl, 7.03.

Rf value was 0.31 on a thin layer chromatography using silica gel glass plate (Art.5721, Merck) in a solvent system which contains 5 parts by volume of the upper layer of $CHCl_3$: methanol:aqueous ammonia:water (4:3:2:1) and 3 parts by volume of methanol, while that of free ribostamycin employed as the control was 0.24.

The starting material ribostamycin 5''-phosphate dihydrate used has been prepared by the procedure disclosed in Applied Microbiology, 16, 1276 (1968), causing the crude enzyme solution of *Pseudomonas aeruginosa* R34R (FERM-P No. 2124) to act upon ribostamycin.

Elemental analysis for $C_{17}H_{35}N_4O_{13}P.2H_2O$: Calcd.: C, 35.79; H, 6.89; N, 9.82; P, 5.43. Found: C, 35.79; H, 6.87; N, 9.82; P, 5.10.

UV: No specific absorption.

Optical rotation: $[\alpha]_D^{24} = +33.3°(c=0.600$ in water).

IR $\nu_{max}^{KBr}$ $cm^{-1}$: 962.

Rf value was 0.25 on a thin layer chromatography using silica gel glass plate (Art.5721, Merck) in a solvent system which contains 5 parts by volume of upper layer of $CHCl_3$:methanol:aqueous ammonia:water (4:3:2:1) and 3 parts by volume of methanol, while that of free ribostamycin employed as control was 0.24.

Tetra-N-acetylribostamycin-5''-phosphate dihydrate.

Elemental analysis for $C_{17}H_{35}N_4O_{13}P.2H_2O$: Calcd.: C, 39.68; H, 6.53; N, 7.40; P, 4.09. Found: C, 39.20; H, 6.52; N, 7.29; P, 4.07.

In 15 parts by volume of water is dissolved 0.15 part of 5''-chloro-5''-deoxyribostamycin and with the addition of 2 parts by volume of Raney nickel and 0.25 part by volume of triethylamine, the system is shaken in hydrogen streams at atmospheric temperature and pressure. After 7 hours, the catalyst is filtered off. Then, the catalyst is washed well with 150 parts by volume of 1N aqueous ammonia and the washing is combined with the filtrate, followed by concentration to about 15 parts by volume. The resulting precipitates are filtered off. The filtrate is then run onto a column of 30 parts by volume of cation exchange resin [Amberlite CG-50($NH_4^+$-form)], and the column is washed with water and eluted with 0 to 0.3N $NH_4OH$ (gradient).

The resulting fraction are combined and concentrated under reduced pressure, whereupon 0.081 part of 5''-deoxyribostamycin dihydrate is obtained.

Elemental analysis for $C_{17}H_{34}O_9N_4.2H_2O$: Calcd.: C, 43.03; H, 8.07; N, 11.81. Found: C, 43.07; H, 7.89; N, 11.51.

Rf value was 0.32 on a thin layer chromatography using silica gel glass plate (Art.5721, Merck) in a solvent system which contained 5 parts by volume of the upper layer of $CHCl_3$:methanol:aqueous ammonia:water (4:3:2:1) and 3 parts by volume of methanol, while that of free ribostamycin employed as the control was 0.24.

NMR($D_2O$) δ ppm: 1.49(3H,d,J=5Hz, $-CH_3$).

EXAMPLE 9

A mixture of 0.5 part of ribostamycin 3'-phosphate trihydrate, 2.7 parts by volume of trimethylsilyl chloride, 1.2 part by volume of hexamethyldisilazane, 2.25 parts by volume of dry pyridine and 0.21 part of triphenylphosphine is heated on an oil bath at 100° to 110° C for 44 hours. After the reaction has been completed, 30 parts by volume of methanol is added to the reaction mixture under ice-cooling, followed by concentration under reduced pressure. The residue is shaken with 100 parts by volume of distilled water and 100 parts by volume of ethyl acetate. The aqueous layer is concentrated and run onto a column of 90 parts by volume of cation exchange resin [Amberlite IRC-50 ($NH_4^+$-form)]. The column is washed with 500 parts by volume of distilled water and, then, eluted with 300 parts by volume of 1N aqueous ammonia. The eluate is concentrated to dryness under reduced pressure to harvest 0.239 part of crude product. This is dissolved in 50 parts by volume of distilled water and run onto a column of 30 parts by volume of cation exchange resin [Amberlite CG-50I ($NH_4^+$-form)].

The column is washed with 100 parts by volume of distilled water and eluted fraction-wise (gradient method) with 0-0.3N aqueous ammonia. The crude product thus obtained is further run onto a column of 20 parts by volume of cation exchange resin [Amberlite CG-50 ($NH_4^+$-form)]. The resulting fractions are combined and concentrated under reduced pressure and lyophilized. Whereupon 0.191 part of 3'-chloro-3'-deoxyribostamycin monohydrate is obtained.

Elemental analysis for $C_{17}H_{33}N_4O_9Cl.H_2O$: Calcd.: C, 41.59; H, 7.18; N, 11.41; Cl, 7.22. Found: C, 41.63; H, 7.10; N, 11.35; Cl, 7.01.

Optical rotation $[\alpha]_D^{24} = +36.8°(c=0.38$ in water).

Rf value was 0.29 on thin layer chromatography using silica gel glass plate (Art.5721, Merck) in a solvent system which contained 5 parts by volume of the upper layer of $CHCl_3$:methanol:aqueous ammonia:water (4:3:2:1) and 3 parts by volume of methanol, while that of free ribostamycin employed as the control was 0.24.

The starting material ribostamycin-3'-phosphate trihydrate used has been prepared by the procedure described in The Journal of Antibiotics 21, 22 (1968), causing the crude enzyme solution of *Escherichia coli* JR66/W677 to act upon ribostamycin.

Elemental analysis for $C_{17}H_{35}N_4O_{13}P\cdot3H_2O$: Calcd.: C, 34.69; H, 7.02; N, 9.52; P, 5.26. Found: C, 34.79; H, 6.86; N, 9.31; P, 5.05.

UV: No specific absorption.

Optical rotation: $[\alpha]_D^{24} = +46.8°$ (c=0.635 in water).

IR $\nu_{max}^{KBr}$ cm$^{-1}$: 955.

Rf value was 0.56 on thin layer chromatography using silica gel glass plate (Art.5721, Merck) in a solvent system which contained 5 parts by volume of the upper layer of CHCl$_3$:methanol:aqueous ammonia:water (4:3:2:1) and 3 parts by volume of methanol, while that of free ribostamycin as the control was 0.24.

Tetra-N-acetylribostamycin-3'-phosphate dihydrate. $C_{25}H_{43}N_4O_{17}P\cdot2H_2O$: Calcd.: C, 40.65; H, 6.41; N, 7.59; P, 4.19. Found: C, 40.84; H, 6.46; N, 7.79; P, 4.30.

In 15 parts by volume of water is dissolved 0.1 part of 3'-deoxy-3'-chlororibostamycin and with the addition of 0.3 part by volume of Raney nickel, the system is shaken in hydrogen streams at atmospheric temperature and pressure. After 4 hours, the catalyst is filtered off. Then, the catalyst is washed well with 100 parts by volume of 1N aqueous ammonia and the washing is combined with the filtrate, followed by concentration. The procedure yields 0.09 part of crude powders. The crude product is dissolved in 20 parts by volume of distilled water and adsorbed on 35 parts by volume of cation exchange resin [Amberlite CG-50I (NH$_4^+$-form)] and eluted with 0 to 0.5N NH$_4$OH (gradient).

The resulting fractions are combined and concentrated under reduced pressure and lyophilized, whereupon 0.068 part of 3'-deoxyribostamycin monohydrate is obtained.

Elemental analysis for $C_{17}H_{34}N_4O_9\cdot H_2O$: Calcd.: C, 44.72; H, 7.94; N, 12.27. Found: C, 44.51; H, 8.08; N, 12.19.

Optical rotation: $[\alpha]_D^{24} = +30.2°$ (c=0.605 in water).

Rf value was 0.29 on a thin layer chromatography using silica gel glass plate (Art 5721, Merck) in a solvent system which contained 5 parts by volume of the upper layer of CHCl$_3$:methanol:aqueous ammonia:water (4:3:2:1) and 3 parts by volume of methanol, while that of free ribostamycin employed as the control was 0.24.

What we claim is:

1. A halogenated aminoglycoside antibiotic selected from the group consisting of 3'-chloro-3'-deoxyxylostasin, 3'-chloro-3'-deoxyneomycin B, 3'-chloro-3'-deoxyneomycin A, 3'-chloro-3'-deoxykanamycin B, 3'-chloro-3'-deoxyparomomycin and 3'-chloro-3'-deoxyribostamycin.

2. 5''-chloro-5''-deoxyribostamycin.

3. A compound as claimed in claim 1, namely, 3'-chloro-3'-deoxyxylostasin.

4. A compound as claimed in claim 1, namely, 3'-chloro-3'-deoxyneomycin B.

5. A compound as claimed in claim 1, namely, 3'-chloro-3'-deoxyneomycin A.

6. A compound as claimed in claim 1, namely, 3'-chloro-3'-deoxykanamycin B.

7. A compound as claimed in claim 1, namely, 3'-chloro-3'-deoxyparomomycin.

8. A compound as claimed in claim 1, namely, 3'-chloro-3'-deoxyribostamycin.

9. 3'-deoxyxylostasin.

10. 3'-deoxyneomycin B.

11. 3'-deoxyribostamycin.

12. A method for the production of deoxyaminoglycoside antibiotics which consists essentially of (1) reacting a phosphorylated aminoglycoside antibiotic with a silylating agent selected from the group consisting of hexamethyldisilazane, trimethylchlorosilane, bis-(trimethylsilyl)-acetamide, bis-(trimethylsilyl)-trifluoroacetamide, trimethylsilylacetamide, N-methyl-N-trimethylsilylacetamide, N-trimethylsilylimidazole, N-(trimethylsilyl)diethylamine and halosilanes, or an acylating agent selected from the group consisting of acetic anhydride, acetyl chloride, benzoyl chloride and benzyloxycarbonyl chloride, (2) halogenating the thus obtained compound with a halogenating agent selected from the group consisting of halosilanes, thionyl chloride, trimethoxymethylphosphonium iodide, phosphorus oxychloride, phosphorus thiooxychloride, phosphorus pentachloride, oxalyl chloride and phosphorus pentabromide, (3) reducing the halogenated derivative, and (4) removing the introduced silyl group by protonization or the introduced acyl group by hydrolysis, removal of said groups being effected between steps (2) and (3), during step (3) or after step (3).

* * * * *